US012631616B2

(12) United States Patent　　(10) Patent No.: US 12,631,616 B2
Kim et al.　　(45) Date of Patent: May 19, 2026

(54) METHOD OF ANALYZING COPOLYCARBONATE

(71) Applicant: LG CHEM, LTD., Seoul (KR)

(72) Inventors: Hyo Yong Kim, Daejeon (KR); Jin Sook Ryu, Daejeon (KR); Sunok Oh, Daejeon (KR); Sung Joon Oh, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1067 days.

(21) Appl. No.: 17/617,196

(22) PCT Filed: Jun. 19, 2020

(86) PCT No.: PCT/KR2020/008009

§ 371 (c)(1),
(2) Date: Dec. 7, 2021

(87) PCT Pub. No.: WO2020/256494

PCT Pub. Date: Dec. 24, 2020

(65) Prior Publication Data

US 2022/0244235 A1　　Aug. 4, 2022

(30) Foreign Application Priority Data

Jun. 20, 2019　(KR) ........................ 10-2019-0073540
Jun. 19, 2020　(KR) ........................ 10-2020-0074897

(51) Int. Cl.
*G01N 33/44*　　(2006.01)
*B01D 15/34*　　(2006.01)
*G01N 24/08*　　(2006.01)

(52) U.S. Cl.
CPC ........... *G01N 33/442* (2013.01); *B01D 15/34* (2013.01); *G01N 24/08* (2013.01)

(58) Field of Classification Search
CPC ....... G01N 33/442; G01N 24/08; B01D 15/34
USPC ........................................................ 528/12
See application file for complete search history.

(56) References Cited

U.S. PATENT DOCUMENTS

| | | | | |
|---|---|---|---|---|
| 5,502,134 A | * | 3/1996 | Okamoto ................. | C08K 7/14 |
| | | | | 524/588 |
| 6,136,521 A | | 10/2000 | Hikosaka et al. | |
| 6,395,862 B1 | | 5/2002 | Lemmon et al. | |
| 8,680,227 B1 | | 3/2014 | Bell et al. | |
| 2012/0202034 A1 | | 8/2012 | Morizur et al. | |
| 2015/0018510 A1 | | 1/2015 | Shidou et al. | |
| 2016/0222191 A1 | | 8/2016 | Sharifi | |
| 2016/0297926 A1 | | 10/2016 | Hwang et al. | |
| 2017/0114184 A1 | * | 4/2017 | Ishikawa .............. | C08G 64/186 |

| | | | |
|---|---|---|---|
| 2018/0044479 A1 | | 2/2018 | Hwang et al. |
| 2018/0051156 A1 | | 2/2018 | Foley et al. |
| 2019/0071539 A1 | | 3/2019 | Ishikawa et al. |
| 2019/0091605 A1 | | 3/2019 | Yamaki et al. |

FOREIGN PATENT DOCUMENTS

| | | | | | |
|---|---|---|---|---|---|
| CN | 1541239 A | | 10/2004 | | |
| CN | 101407450 A | | 4/2009 | | |
| CN | 101415750 A | | 4/2009 | | |
| CN | 104220484 A | | 12/2014 | | |
| CN | 106133026 A | | 11/2016 | | |
| CN | 108554450 A | | 9/2018 | | |
| JP | 2006143882 A | * | 6/2006 | | |
| JP | 2008-31452 A | | 2/2008 | | |
| KR | 10-0459068 B1 | | 12/2004 | | |
| KR | 10-2015-0028359 A | | 3/2015 | | |
| KR | 10-2016-0067731 A | | 6/2016 | | |
| KR | 10-2017-0091506 A | | 8/2017 | | |
| KR | 10-2018-0043683 A | | 4/2018 | | |
| TW | 201333078 A | | 8/2013 | | |
| WO | 1998037120 A1 | | 8/1998 | | |
| WO | WO-02055585 A2 | * | 7/2002 | .......... | C08G 64/307 |
| WO | 2016/089135 A2 | | 6/2016 | | |
| WO | 2017111499 A1 | | 6/2017 | | |
| WO | 2017/158740 A1 | | 9/2017 | | |

OTHER PUBLICATIONS

Morita et al., JP 2006143882 A machine translation in English, Jun. 8, 2006. (Year: 2006).*
Liu et al., Polymer Degradation and Stability, Depolymerization kinectics for thermoplastic polyurethane elastomer degradation in subcritical methanol, vol. 140, Apr. 25, 2017, pp. 126-135.
Pinero et al., Green Chemistry, Chemical recycling of Polycarbonate in a semi-continuous lab-plant. A green Route with methanol and Methanol-water Mixtures, vol. 7, No. 5, Jan. 1, 2005, p. 380-387.
Feng, et al. "Synthesis and Characterization of 3-(2,3-Dihydroxypropoxy)propyl-Terminated Polydimethylsiloxanes", Journal of Applied Polymer Science, 2004, vol. 94, pp. 110-115.
Matsukawa, et al. "Synthesis of α,ω-bis(p-hydroxyphenyl)polysiloxanes", Polymer, 1992, vol. 33, No. 3, pp. 667-670.
Hu, et al. "Alkali-Catalyzed Methanolysis of Polycarbonate. A Study on Recycling of Bisphenol A and Dimethyl Carbonate", Polymer, 1998, vol. 39, No. 16, pp. 3841-3845.

* cited by examiner

*Primary Examiner* — David T Karst

(74) *Attorney, Agent, or Firm* — Bryan Cave Leighton Paisner LLP

(57)　　　　　　　ABSTRACT

Provided is a method of analyzing a copolycarbonate. More particularly, provided is a method of analyzing a copolycarbonate, in which a polysiloxane structure is introduced into the main chain of a polycarbonate, the method capable of more accurately analyzing a weight average molecular weight, a number average molecular weight, and a molecular weight distribution of a polysiloxane-containing aromatic diol compound which is used as a starting material.

8 Claims, No Drawings

METHOD OF ANALYZING COPOLYCARBONATE

BACKGROUND OF THE INVENTION

(a) Field of the Invention

Cross-reference to Related Application

The present application is a National Phase entry pursuant to 35 U.S.C. § 371 of International Application No. PCT/KR2020/008009, filed on Jun. 19, 2020, and claims priority to and the benefit of Korean Patent Application No. 10-2019-0073540, filed on Jun. 20, 2019 and Korean Patent Application No. 10-2020-0074897, filed on Jun. 19, 2020. The disclosures of which are hereby incorporated by reference in their entirety for all purposes as if fully set forth herein.

Technical Field

The present invention relates to a method of analyzing a copolycarbonate.

(b) Description of the Related Art

Polycarbonate resins are prepared by condensation-polymerization of an aromatic diol such as bisphenol A with a carbonate precursor such as a phosgene, and have excellent impact strength, dimensional stability, heat resistance, transparency, etc. Thus, the polycarbonate resins have application in a wide range of uses, such as exterior materials of electrical and electronic products, automobile parts, building materials, optical components, etc.

Recently, in order to apply these polycarbonate resins to more varied fields, many studies have been made to obtain desired physical properties by copolymerizing two or more aromatic diol compounds having different structures from each other and introducing units having different structures into the main chain of the polycarbonate.

Especially, recent studies have been conducted on introducing a polysiloxane structure into the main chain of the polycarbonate.

Physical properties of the polycarbonate are greatly influenced by its molecular weight and molecular weight distribution. Therefore, analysis of the molecular weight of the polycarbonate is the most basic and important analysis in terms of predicting the physical properties of the polymer.

Generally, as a method of analyzing a molecular weight of a polymer such as polycarbonate, an end group analysis, a method of using colligative properties, a light scattering method, a ultracentrifugal method, viscometry, or gel permeation chromatography (GPC) is frequently used.

The most representative method of analyzing a molecular weight of a polymer is gel permeation chromatography, which is one of the most useful methods of measuring a ratio of a relative molecular weight using a standard material, of which a molecular weight is known.

Meanwhile, in the case of a copolycarbonate in which a polysiloxane structure is introduced into the main chain by copolymerizing two or more aromatic diol compounds having different structures from each other, a method of measuring the molecular weights of the diol compounds decomposed by cleaving carbonate bonds of the copolycarbonate may be generally used in order to measure the content and the molecular weight of different repeating units included in the corresponding copolycarbonate. A method of cleaving the carbonate bonds may include thermal pyrolysis, solvolysis using a supercritical fluid (methanol, ethanol, toluene, etc.), cleavage using microwaves, etc. However, in the above cleavage methods, a large amount of energy is used. Therefore, since polysiloxane is also decomposed into polysiloxane units, it is difficult to accurately analyze the content and the molecular weight of the original repeating units.

Alternatively, there is a method of using nuclear magnetic resonance (NMR) without decomposition of the copolycarbonate. When the nuclear magnetic resonance method is used, an average molecular weight of the polysiloxane used in the copolycarbonate may be calculated, but a molecular weight distribution of the polysiloxane, which influences physical properties, may not be determined, and when two or more different polysiloxane structures are introduced, the molecular weights of the respective polysiloxanes may not be determined.

Accordingly, there is a demand for a method of analyzing a polymer, the method capable of accurately analyzing a content ratio, a molecular weight, and a molecular weight distribution of each repeating unit included in copolycarbonate, in which the polysiloxane structure is introduced into the main chain.

SUMMARY OF THE INVENTION

There is provided a method of analyzing a copolycarbonate, in which a polysiloxane structure is introduced into the main chain of a polycarbonate, the method capable of more accurately analyzing a weight average molecular weight, a number average molecular weight, and a molecular weight distribution of a polysiloxane-containing aromatic diol compound which is used as a starting material.

To solve the above problem, there is provided a method of analyzing a copolycarbonate, the method including the steps of reacting the copolycarbonate including a first repeating unit derived from an aromatic diol compound and a second repeating unit derived from a polysiloxane-containing aromatic diol compound with methanol to decompose the copolycarbonate into the aromatic diol compound and the polysiloxane-containing aromatic diol compound; and performing gel permeation chromatography of the decomposed polysiloxane-containing aromatic diol compound.

According to an analysis method of the present invention, with regard to a copolycarbonate, in which a polysiloxane structure is introduced into the main chain, it is possible to more accurately analyze a weight average molecular weight, a number average molecular weight, and a molecular weight distribution of a polysiloxane-containing aromatic diol compound which is used as a starting material.

DETAILED DESCRIPTION OF THE EMBODIMENTS

The present invention may be variously modified and have various forms, and specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, a method of analyzing a copolycarbonate according to one exemplary embodiment of the present invention will be described.

The method of analyzing a copolycarbonate according to a specific embodiment of the present invention can include the steps of reacting the copolycarbonate including a first repeating unit derived from an aromatic diol compound and a second repeating unit derived from a polysiloxane-containing aromatic diol compound with methanol to decompose the copolycarbonate into the aromatic diol compound and the polysiloxane-containing aromatic diol compound; and performing gel permeation chromatography of the decomposed polysiloxane-containing aromatic diol compound.

A polycarbonate is prepared by condensation-polymerization of an aromatic diol compound such as bisphenol A with a carbonate precursor such as a phosgene, and has excellent impact strength, dimensional stability, heat resistance, transparency, etc. Thus, the polycarbonate has application in a wide range of uses, such as exterior materials of electrical and electronic products, automobile parts, building materials, optical components, etc.

To further improve physical properties of the polycarbonate, a polysiloxane structure may be introduced into the main chain of the polycarbonate, and as a result, various physical properties may be improved.

Meanwhile, the physical properties of the polycarbonate are greatly influenced by its molecular weight and molecular weight distribution. Therefore, analysis of the molecular weight of the polycarbonate is the most basic and important analysis in terms of predicting the physical properties of the polymer.

However, in the case of the copolycarbonate, in which a polysiloxane structure is introduced into the main chain by copolymerizing two or more aromatic diol compounds having different structure from each other, it is not easy to accurately analyze the molecular weight of only the repeating unit containing the polysiloxane structure.

Alternatively, there is a method of analyzing the copolycarbonate using nuclear magnetic resonance (NMR) without decomposition of the copolycarbonate. However, when two or more different kinds of polysiloxane structures are introduced into the copolycarbonate, it is difficult to distinguish respective polysiloxane structures from each other, and although analysis of the molecular weight is possible, it is impossible to analyze the molecular weight distribution, which has a large influence on physical properties of the polymer.

Accordingly, it was found that the copolycarbonate including the first repeating unit derived from the aromatic diol compound and the second repeating unit derived from the polysiloxane-containing aromatic diol compound is reacted with methanol to decompose the copolycarbonate into the aromatic diol compound and the polysiloxane-containing aromatic diol compound which are original starting materials, and the molecular weight of the decomposed polysiloxane-containing aromatic diol compound can be measured by gel permeation chromatography (GPC), leading to the present invention.

The first repeating unit derived from the aromatic diol compound is formed by reacting the aromatic diol compound with a carbonate precursor, and the first repeating unit is distinguished from the second repeating unit described below in that it does not include polysiloxane.

The first repeating unit derived from the aromatic diol compound can be specifically represented by Chemical Formula 1:

[Chemical Formula 1]

in Chemical Formula 1, $R_1$ to $R_4$ are each independently hydrogen, $C_{1-10}$ alkyl, $C_{1-10}$ alkoxy, or halogen, and Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

In Chemical Formula 1, preferably, $R_1$ to $R_4$ are each independently hydrogen, methyl, chloro, or bromo.

Further, Z is preferably linear or branched $C_{1-10}$ alkylene unsubstituted or substituted with phenyl, and more preferably, methylene, ethane-1,1-diyl, propane-2,2-diyl, butane-2,2-diyl, 1-phenylethane-1,1-diyl, or diphenylmethylene. Further, Z is preferably cyclohexane-1,1-diyl, O, S, SO, $SO_2$, or CO.

Preferably, the repeating unit represented by Chemical Formula 1 can be derived from one or more aromatic diol compounds selected from the group consisting of bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl)sulfide, bis(4-hydroxyphenyl)ketone, 1,1-bis(4-hydroxyphenyl)ethane, bisphenol A, 2,2-bis(4-hydroxyphenyl)butane, 1,1-bis(4-hydroxyphenyl)cyclohexane, 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, 1,1-bis(4-hydroxyphenyl)-1-phenylethane, bis(4-hydroxyphenyl)diphenylmethane, and α,ω-bis[3-(o-hydroxyphenyl)propyl]polydimethylpolysiloxane.

The description 'derived from an aromatic diol compound' means that a hydroxy group of the aromatic diol compound and a carbonate precursor are reacted to form the repeating unit represented by Chemical Formula 1.

The repeating unit represented by Chemical Formula 1 is derived from an aromatic diol compound represented by the following Chemical Formula 1-1:

[Chemical Formula 1-1]

in Chemical Formula 1-1, $R_1$ to $R_4$, and Z are the same as defined in Chemical Formula 1.

For example, when bisphenol A, which is an aromatic diol compound, and triphosgene, which is a carbonate precursor, are polymerized, the repeating unit represented by Chemical Formula 1 can be represented by the following Chemical Formula 1-2:

[Chemical Formula 1-2]

The carbonate precursor can include one or more selected from the group consisting of dimethyl carbonate, diethyl carbonate, dibutyl carbonate, dicyclohexyl carbonate, diphenyl carbonate, ditolyl carbonate, bis(chlorophenyl)carbonate, di-m-cresyl carbonate, dinaphthyl carbonate, bis(diphenyl)carbonate, phosgene, triphosgene, diphosgene, bromophosgene and bishaloformate. Preferably, triphosgene or phosgene can be used.

The structure of the polysiloxane-containing aromatic diol compound which is an analysis target of the present invention is not particularly limited, as long as a polysiloxane residue is included in the compound, and a bond cleaved by alkali-catalyzed alcoholysis, for example, an ester bond is not included. When the compound includes the bond cleaved by alkali-catalyzed alcoholysis, it may be decomposed by methanolysis described below. Therefore, it is difficult to accurately measure the molecular weight by applying the analysis method of the present invention alone. However, when the structure of the polysiloxane-containing compound is analyzed by applying NMR analysis in combination with the analysis method of the present invention, it is possible to analyze the molecular weights of the respective repeating units.

According to one exemplary embodiment of the present invention, the second repeating unit derived from the polysiloxane-containing aromatic diol compound can be represented by the following Chemical Formula 2 to Chemical Formula 5, but is not limited thereto:

[Chemical Formula 2]

in Chemical Formula 2, $X_1$ is each independently $C_{1-10}$ alkylene, $R_5$ is each independently hydrogen; unsubstituted or oxiranyl, oxiranyl-substituted $C_{1-10}$ alkoxy, or $C_{6-20}$ aryl-substituted $C_{1-15}$ alkyl; halogen; $C_{1-10}$ alkoxy; allyl; $C_{1-10}$ haloalkyl; or $C_{6-20}$ aryl, and n is an integer of 10 to 200,

[Chemical Formula 3]

in Chemical Formula 3, $X_2$ is each independently $C_{1-10}$ alkylene, $Y_1$ is each independently hydrogen, $C_{1-6}$ alkyl, halogen, hydroxy, $C_{1-6}$ alkoxy, or $C_{6-20}$ aryl, $R_6$ is each independently hydrogen; unsubstituted or oxiranyl, oxiranyl-substituted $C_{1-10}$ alkoxy, or $C_{6-20}$ aryl-substituted $C_{1-15}$ alkyl; halogen; $C_{1-10}$ alkoxy; allyl; $C_{1-10}$ haloalkyl; or $C_{6-20}$ aryl, and m is an integer of 10 to 200,

[Chemical Formula 4]

in Chemical Formula 4, $X_3$ is each independently $C_{1-10}$ alkylene, $Y_2$ is each independently hydrogen, $C_{1-6}$ alkyl, halogen, hydroxy, $C_{1-6}$ alkoxy, or $C_{6-20}$ aryl,-

$R_7$ is each independently hydrogen; unsubstituted or oxiranyl, oxiranyl-substituted $C_{1-10}$ alkoxy, or $C_{6-20}$ aryl-substituted $C_{1-15}$ alkyl; halogen; $C_{1-10}$ alkoxy; allyl; $C_{1-10}$ haloalkyl; or $C_{6-20}$ aryl, and k is an integer of 10 to 200,

[Chemical Formula 5]

in Chemical Formula 5, $X_4$ is each independently $C_{1-10}$ alkylene,

Y is $C_{1-10}$ alkylene or $C_{6-20}$ arylene, $R_8$ is each independently hydrogen; unsubstituted or oxiranyl, oxiranyl-substituted $C_{1-10}$ alkoxy, or $C_{6-20}$ aryl-substituted $C_{1-15}$ alkyl; halogen; $C_{1-10}$ alkoxy; allyl; $C_{1-10}$ haloalkyl; or $C_{6-20}$ aryl, and q is an integer of 10 to 200.

In Chemical Formula 2, preferably, $X_1$ is each independently $C_{2-10}$ alkylene, more preferably, $C_{2-4}$ alkylene, and most preferably, propane-1,3-diyl.

Preferably, $R_5$ is each independently hydrogen, methyl, ethyl, propyl, 3-phenylpropyl, 2-phenylpropyl, 3-(oxiranyl-methoxy)propyl, fluoro, chloro, bromo, iodo, methoxy, ethoxy, propoxy, allyl, 2,2,2-trifluoroethyl, 3,3,3-trifluoro-propyl, phenyl, or naphthyl. Preferably, $R_5$ is each independently $C_{1-10}$ alkyl, more preferably, $C_{1-6}$ alkyl, much more preferably, $C_{1-3}$ alkyl, and most preferably, methyl.

Preferably, n is an integer of 10 or more, 15 or more, 20 or more, 25 or more, 30 or more, 31 or more, or 32 or more, and 50 or less, 45 or less, 40 or less, 39 or less, 38 or less, or 37 or less.

In Chemical Formula 3, preferably, $X_2$ is each independently $C_{2-10}$ alkylene, more preferably, $C_{2-6}$ alkylene, and most preferably isobutylene.

Preferably, $Y_1$ is hydrogen.

Preferably, $R_6$ is each independently hydrogen, methyl, ethyl, propyl, 3-phenylpropyl, 2-phenylpropyl, 3-(oxiranyl-methoxy)propyl, fluoro, chloro, bromo, iodo, methoxy, ethoxy, propoxy, allyl, 2,2,2-trifluoroethyl, 3,3,3-trifluoro-propyl, phenyl, or naphthyl. Preferably, $R_6$ is each independently $C_{1-10}$ alkyl, more preferably, $C_{1-6}$ alkyl, much more preferably, $C_{1-3}$ alkyl, and most preferably, methyl.

Preferably, m is an integer of 30 or more, 35 or more, 40 or more, 45 or more, 46 or more, 47 or more, or 48 or more, and 70 or less, 65 or less, 60 or less, 55 or less, 54 or less, 53 or less, or 52 or less.

Preferably, the repeating unit represented by Chemical Formula 2 can be represented by the following Chemical Formula 2-2:

[Chemical Formula 2-2]

in Chemical Formula 2-2, $R_5$ and n are the same as defined in Chemical Formula 2. Preferably, $R_5$ is methyl.

Preferably, the repeating unit represented by Chemical Formula 3 can be represented by the following Chemical Formula 3-2:

[Chemical Formula 3-2]

in Chemical Formula 3-2, $R_6$ and m are the same as defined in Chemical Formula 3. Preferably, $R_6$ is methyl.

The repeating unit represented by Chemical Formula 2 and the repeating unit represented by Chemical Formula 3 are derived from a polysiloxane compound represented by the following Chemical Formula 2-1 and a polysiloxane compound represented by the following Chemical Formula 3-1, respectively:

[Chemical Formula 2-1]

in Chemical Formula 2-1, $X_1$, $R_5$, and n are the same as defined in Chemical Formula 2,

[Chemical Formula 3-1]

in Chemical Formula 3-1, $X_2$, $Y_1$, $R_6$, and m are the same as defined in Chemical Formula 3.

The description 'derived from a polysiloxane compound' means that a hydroxy group of each polysiloxane compound and a carbonate precursor are reacted to form the repeating units represented by Chemical Formulae 2 to 5, respectively. Further, the carbonate precursors that can be used in the formation of the repeating units of Chemical Formulae 2 to 5 are the same as described in the carbonate precursor that can be used in the formation of the repeating unit of Chemical Formula 1 described above.

As described above, the copolycarbonate including the first repeating unit and the second repeating unit is reacted with methanol to decompose the copolycarbonate into the aromatic diol compound and the polysiloxane-containing aromatic diol compound which are starting materials.

According to one exemplary embodiment of the present invention, when the copolycarbonate is reacted with methanol under alkaline conditions, it can be decomposed by an alkali-catalyzed alcoholysis reaction into the aromatic diol compound and the polysiloxane-containing aromatic diol compound, which are starting materials, respectively. In other words, according to the alkali-catalyzed alcoholysis reaction, the copolycarbonate can be decomposed into the aromatic diol compound and the polysiloxane-containing aromatic diol compound.

More specifically, an alkali is dissolved in methanol to prepare an alkali hydroxide solution. The alkali used herein may be, for example, sodium hydroxide (NaOH), potassium hydroxide (KOH), or ammonium hydroxide (NH4OH)."; and the present invention is not limited thereto.

When the alkali hydroxide solution thus prepared is reacted with copolycarbonate, the carbonate bond is decomposed by the alkali-catalyzed alcoholysis reaction, and as a result, the copolycarbonate can be decomposed into the aromatic diol compound and the polysiloxane-containing aromatic diol compound. In this regard, the temperature of the alkali-catalyzed alcoholysis reaction can be 40° C. to 80° C., or 60° C. to 70° C. In addition, the reaction time is not particularly limited, as long as it is a time for which the copolycarbonate can be completely decomposed. However, the reaction can be performed for, for example, 1 hr to 10 hr, or 2 hr to 8 hr, and in order to facilitate the reaction, the reaction can be performed under stirring using a magnetic bar, etc.

The reaction can be performed in a hydrocarbon-based solvent. For example, aliphatic hydrocarbon solvents having 5 to 12 carbon atoms, such as pentane, hexane, heptane, nonane, decane, and isomers thereof, aromatic hydrocarbon solvents such as toluene and benzene, chlorine-substituted hydrocarbon solvents such as dichloromethane and chlorobenzene, etc. can be used, but the present invention is not limited thereto.

According to the present invention, as described above, the copolycarbonate and methanol are reacted to decompose the copolycarbonate into the aromatic diol compound and the polysiloxane-containing aromatic diol compound, and then the decomposition product is quenched using liquid nitrogen without a separate extraction and/or purification process, and is diluted with a solvent such as THF, followed by GPC. Bisphenol, dimethyl carbonate, methanol, NaOH, and the like are present in the decomposition product, but a polymeric material which can be identified through GPC is only the polysiloxane-containing aromatic diol compound, and therefore, no additional extraction and/or purification processes are required. As described, since no separate extraction process is required after decomposition, the molecular weight and the molecular weight distribution of the polysiloxane-containing aromatic diol compound in copolycarbonate can be more accurately analyzed while the process is simplified.

Alternatively, after the reaction is completed, when the mixture containing the aromatic diol compound and the polysiloxane-containing aromatic diol compound is quenched with distilled water and/or toluene, and left at room temperature, it is separated into the crystalline aromatic diol compound and the amorphous polysiloxane-containing aromatic diol compound, and the separated polysiloxane-containing aromatic diol compound can be extracted, followed by GPC.

Next, the extracted polysiloxane-containing aromatic diol compound is subjected to gel permeation chromatography (GPC), and a GPC curve graph is obtained.

The weight average molecular weight, number average molecular weight, and molecular weight distribution of the extracted polysiloxane-containing aromatic diol compound can be obtained by the GPC.

The GPC is a kind of liquid-solid-phase liquid chromatography using an elution method, in which a large molecule is first eluted due to the size of a solute molecule. When molecules have the same size, they can be eluted at the same position, regardless of the type of solutes or the type of functional groups.

In the GPC, a mobile phase is based on a liquid chromatography grade, and can be used after filtration, and a solvent having a high viscosity is used by raising its temperature, and the solvent can be appropriately selected, taking the temperature of each solvent into consideration. When a polar solvent is used as the solvent, it is necessary to use an additive to prevent formation of micelles.

The type of a column filler used in the GPC is not particularly limited, but, for example, a rigid or semi-rigid, cross-linked macromolecular polymer, and glass or silica with a controlled pore size can be used. The filler can withstand a pressure of up to 3000 psi, and aqueous solutions and various polar organic solvents can be used. Porous glass and silica can be used after being prepared to have various pore sizes. These fillers are chemically resistant to pH of 10 or less, and are resistant to aqueous solutions and polar organic solvents. In the case of using a non-polar solvent, the surface must be deactivated by silylation in order to avoid irreversible retention by polar solutes. The packing volume can be maintained constant at a high flow rate and high pressure.

The GPC device is not particularly limited, but can consist of, for example, a pump, a sample injector, and a detector.

The pump must be able to maintain a constant flow rate, and requires reproducibility of the flow rate, particularly, reproducibility independent of viscosity of the polymer. In addition, when analysis is performed at a high temperature, it is generally required to raise the temperature to 55° C. or higher.

The amounts of the sample and the standard material injected into the sample injector should be equal, and in general, Rheodyne, U6K, auto injector type, etc. can be used. The injection amounts of the sample and the standard material are usually about 50 μl to 100 μl per column.

The type of the detector is not particularly limited, but for example, a differential refractometer and a spectrophotometric detector operating in the ultraviolet and infrared regions can be used. The detector has an operating volume of 1 ml to 10 ml in an exclusion tube having a length of 3 m to 6 m, and the analysis time is usually less than 30 minutes.

With respect to the copolycarbonate into which the polysiloxane structure is introduced by the above described method, the weight average molecular weight, the number average molecular weight, and the molecular weight distribution of the polysiloxane-containing aromatic diol compound used as a starting material can be accurately analyzed.

Meanwhile, according to one exemplary embodiment of the present invention, nuclear magnetic resonance (NMR) can be additionally performed on the copolycarbonate into which the polysiloxane structure is introduced. The structures of the repeating units constituting the copolycarbonate can be inferred by NMR analysis, and therefore, even when the repeating unit of the copolycarbonate to be analyzed by the present invention, i.e., the polysiloxane-containing aromatic diol compound includes a functional group decomposable in methanol, the weight average molecular weight, the number average molecular weight, and the molecular weight distribution of the repeating unit can be obtained by taking together the structure analyzed by NMR.

The present invention will be described in more detail with reference to the following exemplary embodiments. However, the following exemplary embodiments are for illustrative purposes only, and the scope of the present invention is not intended to be limited by the following exemplary embodiments.

12

EXAMPLE

Preparation Example of Copolycarbonate

Preparation Example 1

A copolycarbonate including a first repeating unit derived from bisphenol A (BPA) of LG Chem, Ltd. and a second repeating unit derived from a polysiloxane-containing aromatic diol compound having the following structural formula (including polysiloxane-containing aromatic diol compound in an amount of 7% by weight, based on the total weight of the copolycarbonate) was prepared.

The following polysiloxane-containing aromatic diol compound used as a starting material had a weight average molecular weight of 4,830 g/mol, a number average molecular weight of 3,300 g/mol, and a molecular weight distribution (Mw/Mn) of 1.47.

Preparation Example 2

Copolycarbonate FG1700 of Idemitsu Co., including a repeating unit derived from a polysiloxane-containing aromatic diol compound, was prepared.

Preparation Example 3

Copolycarbonate EXL1414 of Sabic Corp., including a repeating unit derived from a polysiloxane-containing aromatic diol compound, was prepared.

Preparation Example 4

Copolycarbonate 3022PJ of Samyang Corp., including a repeating unit derived from a polysiloxane-containing aromatic diol compound, was prepared.

The repeating units of Preparation Examples 2 to 4 were structures analyzed by NMR.

EXAMPLE

Example 1

1 g of the copolycarbonate pellet of Preparation Example 1 was dissolved in 2 ml of toluene, and 34 mg of NaOH was dissolved in 1 ml of methanol, and these two solutions were mixed. The mixed solution was heated at 60° C. under stirring, and allowed to react for 6 hr until no pellet forms were left.

After the decomposition reaction was completed, the decomposition product including the polysiloxane-containing diol compound was quenched in liquid nitrogen at −196° C., and 4 g of the decomposition product was diluted in 200 ml of a tetrahydrofuran (THF) solvent to prepare a sample of about 20,000 ppm, of which molecular weight was measured using a Agilent 1200 series GPC system through an RI detector at a flow rate of 1 ml/min. To calculate the molecular weight of the sample, eight PS standards were used to prepare a calibration curve, and based on the curve, the weight average molecular weight, the number average molecular weight, and the molecular weight distribution of the sample were determined and shown in Table 1 below.

TABLE 1

| | Weight average molecular weight (Mw, unit: g/mol) | Number average molecular weight (Mn, unit: g/mol) | Molecular weight distribution, (PDI Mw/Mn) |
|---|---|---|---|
| Reference Example (polysiloxane-containing aromatic diol compound used as starting material) | 4,830 | 3,300 | 1.47 |
| Example 1 | 5,050 | 3,340 | 1.51 |

Referring to Table 1, the weight average molecular weight, the number average molecular weight, and the molecular weight distribution of the decomposed polysiloxane-containing aromatic diol compound with respect to the weight average molecular weight, the number average molecular weight, and the molecular weight distribution of the polysiloxane-containing aromatic diol compound which is a starting material before polymerization were about 104%, about 101%, and about 103%, respectively, indicating that the error was within 5%, as compared with the measured values of the actual starting material.

Examples 2 to 4

The copolycarbonates of Preparation Examples 2 to 4 were decomposed in the same manner as in Example 1.

4 g of the decomposition product including the decomposed polysiloxane-containing diol compound was diluted in 200 ml of a tetrahydrofuran (THF) solvent to prepare a sample of about 20,000 ppm, of which molecular weight was measured using a Agilent 1200 series GPC system through an RI detector at a flow rate of 1 ml/min. To calculate the molecular weight of the sample, eight PS standards were used to prepare a calibration curve, and based on the curve, the weight average molecular weight, the number average molecular weight, and the molecular weight distribution of each sample were determined.

The structures of the copolycarbonates of Preparation Examples 2 to 4 were analyzed by $^1$H-NMR using Varian 500 MHz, and the number average molecular weight of the polysiloxane-containing diol compound was measured.

For the analysis of the molecular weight of the polysiloxane-containing diol compound by $^1$H-NMR, the number of the repeating unit derived from the polysiloxane-containing diol compound was calculated using proton, and multiplied by the molecular weight of one repeating unit, which can be determined as the number average molecular weight.

The weight average molecular weight and the number average molecular weight, which were measured for the polysiloxane-containing aromatic diol compounds of Examples 2 to 4 by GPC and NMR, respectively, were compared in Table 2 below.

TABLE 2

| | Weight average molecular weight (unit: g/mol) as measured by GPC | Number average molecular weight (unit: g/mol) as measured by NMR | Number average molecular weight (unit: g/mol) as measured by GPC | Molecular weight distribution as measured by GPC |
|---|---|---|---|---|
| Example 2 | 6,190 | 5,750 | 4,600 | 1.35 |
| Example 3 | 5,660 | 4,000 | 3,990 | 1.42 |
| Example 4 | 3,170 | 4,770 | 2,470 | 1.28 |

Referring to Table 2, the number average molecular weights of the polysiloxane-containing aromatic diol compounds decomposed according to the method of the present invention were about 80%, about 99.8%, and about 51.8% of those of the copolycarbonates including different structures of polysiloxane, as measured by NMR.

In the case of Example 4, the number average molecular weight measured by GPC was about 51% of the number average molecular weight measured by NMR, which can be attributed to that the polysiloxane-containing aromatic diol compound includes ester bonds during analysis of its structure by NMR, and these ester bonds are also decomposed during methanolysis. Accordingly, considering the decomposition of the ester bonds, it is almost consistent with the number average molecular weight measured by NMR.

15

What is claimed is:

1. A method of analyzing a copolycarbonate, the method comprising:

reacting the copolycarbonate including a first repeating unit derived from an aromatic diol compound and a second repeating unit derived from a polysiloxane-containing aromatic diol compound with methanol to decompose the copolycarbonate into the aromatic diol compound and the polysiloxane-containing aromatic diol compound; and performing gel permeation chromatography (GPC) of the decomposed polysiloxane-containing aromatic diol compound after the reacting step without a separate extraction and/or purification process, wherein the step of reacting the copolycarbonate with methanol includes the steps of dissolving an alkali salt in methanol to prepare an alkali hydroxide solution; and reacting the prepared alkali hydroxide solution with the copolycarbonate to perform an alkali-catalyzed alcoholysis reaction, wherein the alkali-catalyzed alcoholysis reaction is performed at 40° C. to 70° C., and wherein the step of performing GPC of the decomposed polysiloxane-containing aromatic diol compound is performed by quenching a decomposition product including the decomposed polysiloxane-containing aromatic diol compound using liquid nitrogen and then diluting the product, followed by GPC.

2. The method of claim 1, wherein the first repeating unit is represented by Chemical Formula 1:

[Chemical Formula 1]

wherein, in Chemical Formula 1, $R_1$ to $R_4$ are each independently hydrogen, $C_{1-10}$ alkyl, $C_{1-10}$ alkoxy, or halogen, and Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

3. The method of claim 2, wherein the repeating unit represented by Chemical Formula 1 is derived from an aromatic diol compound represented by Chemical Formula 1-1:

16

[Chemical Formula 1-1]

wherein, in Chemical Formula 1-1, $R_1$ to $R_4$ and Z are the same as defined in Chemical Formula 1.

4. The method of claim 1, wherein the second repeating unit is represented by any one of Chemical Formula 2 to Chemical Formula 5:

[Chemical Formula 2]

wherein, in Chemical Formula 2, $X_1$ is each independently $C_{1-10}$ alkylene, $R_5$ is each independently hydrogen; $C_{1-15}$ alkyl which is unsubstituted or substituted with oxiranyl, oxiranyl-substituted $C_{1-10}$ alkoxy, or $C_{6-20}$ aryl; halogen; $C_{1-10}$ alkoxy; allyl; $C_{1-10}$ haloalkyl; or $C_{6-20}$ aryl, and n is an integer of 10 to 200,

[Chemical Formula 3]

wherein, in Chemical Formula 3, $X_2$ is each independently $C_{1-10}$ alkylene, $Y_1$ is each independently hydrogen, $C_{1-6}$ alkyl, halogen, hydroxy, $C_{1-6}$ alkoxy, or $C_{6-20}$ aryl, $R_6$ is each independently hydrogen; $C_{1-15}$ alkyl which is unsubstituted or substituted with oxiranyl, oxiranyl-substituted $C_{1-10}$ alkoxy, or $C_{6-20}$ aryl; halogen; $C_{1-10}$ alkoxy; allyl; $C_{1-10}$ haloalkyl; or $C_{6-20}$ aryl, and m is an integer of 10 to 200,

[Chemical Formula 4]

wherein, in Chemical Formula 4, $X_3$ is each independently $C_{1-10}$ alkylene, $Y_2$ is each independently hydrogen, $C_{1-6}$ alkyl, halogen, hydroxy, $C_{1-6}$ alkoxy, or $C_{6-20}$ aryl, $R_7$ is each independently hydrogen; $C_{1-15}$ alkyl which is unsubstituted or substituted with oxiranyl, oxiranyl-substituted $C_{1-10}$ alkoxy, or $C_{6-20}$ aryl; halogen; $C_{1-10}$ alkoxy; allyl; $C_{1-10}$ haloalkyl; or $C_{6-20}$ aryl, and k is an integer of 10 to 200,

[Chemical Formula 5]

wherein, in Chemical Formula 5, $X_4$ is each independently $C_{1-10}$ alkylene, Y is $C_{1-10}$ alkylene or $C_{6-20}$ arylene, $R_8$ is each independently hydrogen; $C_{1-15}$ alkyl which is unsubstituted or substituted with oxiranyl, oxiranyl-substituted $C_{1-10}$ alkoxy, or $C_{6-20}$ aryl; halogen; $C_{1-10}$ alkoxy; allyl; $C_{1-10}$ haloalkyl; or $C_{6-20}$ aryl, and q is an integer of 10 to 200.

5. The method of claim 4, wherein the repeating unit represented by Chemical Formula 2 is derived from a polysiloxane compound represented by Chemical Formula 2-1:

[Chemical Formula 2-1]

wherein, in Chemical Formula 2-1, $X_1$, $R_5$ and n are the same as defined in Chemical Formula 2.

6. The method of claim 4, wherein the repeating unit represented by Chemical Formula 3 is derived from a polysiloxane compound represented by Chemical Formula 3-1:

[Chemical Formula 3-1]

wherein, in Chemical Formula 3-1, $X_2$, $Y_1$, $R_6$ and m are the same as defined in Chemical Formula 3.

7. The method of claim 1, wherein a weight average molecular weight, a number average molecular weight, and a molecular weight distribution of the decomposed polysiloxane-containing aromatic diol compound are obtained by the gel permeation chromatography.

8. The method of claim 1, further comprising the step of performing nuclear magnetic resonance (NMR) of the copolycarbonate.

* * * * *